United States Patent [19]
Mensor, Jr.

[11] Patent Number: 4,993,950
[45] Date of Patent: Feb. 19, 1991

[54] COMPLIANT KEEPER SYSTEM FOR FIXED REMOVABLE BRIDGEWORK AND MAGNETICALLY RETAINED OVERDENTURES

[76] Inventor: Merrill C. Mensor, Jr., 11670 St. Bernard, Tahoe-Donner, Truckee, Calif. 95737

[21] Appl. No.: 554,151

[22] Filed: Jul. 13, 1990

Related U.S. Application Data

[63] Continuation of Ser. No. 209,324, Jun. 20, 1988, abandoned.

[51] Int. Cl.⁵ .............................................. A61C 8/00
[52] U.S. Cl. .................................. 433/173; 433/174; 433/189
[58] Field of Search ............... 433/169, 170, 173, 174, 433/189

[56] References Cited

U.S. PATENT DOCUMENTS

| | | | |
|---|---|---|---|
| 4,447,210 | 5/1984 | Hidaka et al. | 433/169 X |
| 4,488,875 | 12/1984 | Nizmick | 433/173 |
| 4,568,285 | 2/1986 | Chiaramonte et al. | 433/169 X |
| 4,626,213 | 12/1986 | Shiner et al. | 433/189 X |
| 4,626,214 | 12/1986 | Artal | 433/169 X |
| 4,631,031 | 12/1986 | Richter | 433/173 |
| 4,682,951 | 7/1987 | Linkow | 433/173 |
| 4,746,293 | 5/1988 | Lundgren et al. | 433/169 X |
| 4,756,689 | 7/1988 | Lundgren et al. | 433/169 X |
| 4,815,975 | 3/1989 | Garrel et al. | 433/189 |
| 4,842,518 | 6/1989 | Linkow et al. | 433/174 |
| 4,872,839 | 10/1989 | Brajnovic | 433/173 |
| 4,881,897 | 11/1989 | Franek et al. | 433/169 |

FOREIGN PATENT DOCUMENTS

| | | | |
|---|---|---|---|
| 0289892 | 11/1988 | European Pat. Off. | 433/189 |
| 2598314 | 11/1987 | France | 433/189 |

Primary Examiner—Robert P. Swiatek
Assistant Examiner—Nicholas A. Lucchesi
Attorney, Agent, or Firm—Jackson & Jones

[57] ABSTRACT

A dental connector structure has a first, transmucosal cuff member which is attached to the jaw bone or tooth root through an implant fixture embedded in the bone or tooth root, and a second, keeper member to which a denture is attached. The second keeper member is removably mounted to the transmucosal cuff. A resilient, elastic member, such as an O ring, is disposed between the transmucosal cuff and the second, keeper member to permit selected limited but substantially universal motion of the keeper member relative to the transmucosal cuff, and to absorb forces transmitted by the denture through the keeper member towards the underlying bone or root structure. The resilient elastic member also keeps the transmucosal cuff and the second, keeper member from contact with one another, and thereby minimizes corrosion. The denture includes a magnetic skirt that limits the lateral movement of the denture and the keeper.

18 Claims, 3 Drawing Sheets

COMPLIANT KEEPER SYSTEM FOR FIXED REMOVABLE BRIDGEWORK AND MAGNETICALLY RETAINED OVERDENTURES

This application is a continuation of Ser. No. 208,324, now abandoned, filed June 20, 1988.

BACKGROUND OF THE INVENTION

1. Field of the Invention

The present invention is in the field of denture retention. More specifically, the present invention is directed to a connector-support structure which with or without magnets anchors overdentures to implant fixtures which are themselves embedded within the jaw bone or tooth root of a person, and cushions the bone or tooth root from masticatory force loads generated by the dentures.

2. Brief Description of the Prior Art

Implant fixtures embedded in the jaw bone or in the tooth root, and connectors removably mounted to the implant fixtures, to provide support for complete and partial dentures are known in the prior art. The dentures, which include one or more false teeth, are affixed, usually in a removable manner, to the connectors. There is a relatively large number of United States and foreign patent disclosures, articles and publications which describe various ways for affixing the overlying dentures to the underlying implant fixtures.

More specifically, the following United States and foreign patents, articles and publications describe various structures wherein magnets are employed to attach the removable dentures to the bone- or tooth root embedded implants: U.S. Pat. Nos. 4,508,507, 4,431,419, 4,626,213, 4,209,905, 4,184,252, 4,214,366, Australian Provisional Patent Specification titled "Magnet Structure" by A. R. Gillings, French Patent Nos. 73.12280 and 75 12748, German Published Patent Application No. 2201415, an article titled "Retentive characteristics of different magnetic systems for dental applications" by Ron Highton et al. in THE JOURNAL OF PROSTHETIC DENTISTRY Volume 56 pp 104-106, Jul. 1986, an article titled "A magnetic attachment for overdentures" by H. Sasaki et al. in THE JOURNAL OF PROSTHETIC DENTISTRY Volume 51 pp 450-455 (1984), a publication titled "THE USE OF RARE EARTH MAGNETIC ASSEMBLIES FOR RETENTION OF DENTAL PROSTHETICS" by T. R. Jackson and a publication titled "MAGNETIC RETENTION UNITS FOR OVERLAY DENTURES" BY B. R. D. Gillings.

U.S. Pat. No. 3,787,975, describes a bone or root canal embedded implant which utilizes a mechanical device, including a socket and a matching ball, for removably attaching the denture to the anchor. A device of related construction, well known in the art under the trade name ZEST of Zest Anchors Inc. of San Diego, Calif., uses a bone or tooth root embedded implant fixture, a connector having a transmucosal cuff including an interior socket, and a keeper member having a ball which fits into the socket, for retaining dentures in the patient's mouth. The keeper member utilizes a strong permanent magnet in the denture to hold the denture.

Other references related to dental prostheses or tissue integrated prostheses include U.S. Pat. Nos. 4,261,350, 4,330,891, British Patent Specification No. 1291 470 and the article titled "BIOPHYSIKALISCHER BEITRAG ZUR PROBLEMATIK STARR ABGESTUTZTER FREIENDPROTHESEN" by H. Rehm at al., DZZ 17 1962 pp 963-975.

It has been recognized in the prior art, that mastication (chewing) subjects a person's teeth, underlying tooth roots, tissue and bone structure to significant forces. Normal, healthy teeth and tissue structure are capable of resiliently yielding under the masticatory forces, and accommodate and absorb these forces without harmful effect. For artificial teeth, and for the underlying implanted fixtures and bone structure, the masticatory forces, however, present a significant problem, and often cause patient discomfort and deterioration of the fixation of the implant fixture in the bone or in the tooth root.

The following articles, publications discuss the nature and magnitude of masticatory forces and their effect on dental prostheses: "Tissue-Integrated Prosthesis" by Branemark/Zarb/Albrektsson (Quintessence Books) pages 123-128; "The Bar Joint Denture" by E. Dolder and G. T. Durrer (Quintessence Books) 1978, pages 95-102; "Precision Work for Partial dentures" by A. Steiger et al. pages 143-145. The last mentioned publication discloses that a healthy human tooth has a resiliency of approximately 0.1 mm in its socket, and that healthy mucous tissue provides a resiliency of approximately 4 to 20 times greater than the resiliency of the tooth in the socket. Conventional rigid prosthetic dental structures, on the other hand, provide virtually zero resiliency.

In fact, and in sharp contrast with the resiliency of natural healthy teeth, there have only been ineffectual attempts in the prior art to provide a limited degree of freedom of motion and force absorbing capability to dental prosthetic structures.

For example, the prior art device known in the art under the ZEST name employs a socket and ball type attachment of the dentures to the underlying implant fixture. By its nature, the socket and ball joint provides a slight degree of freedom of motion and a slight degree of vertical resiliency.

A publication titled "Stress Absorbing Elements in Implants" prepared by Core-Vent Corporation of Encino, Calif., discusses stress absorption in dental prostheses by using plastic screws in the "anchoring" structures, and by the use of intermediate plastic (polyoxymethylene, DELRIN) connector plates such as employed by an IMZ dental implant system and distributed by Interpore International of Irvine, Calif. This publication actually expresses doubt regarding the practical utility of these prior art attempts to provide resiliency to dental prostheses.

In light of the foregoing, there is a need in the prior art for connectors or anchors for dental prostheses, which have significant ability to absorb masticatory forces, and provide a desirable freedom of motion to the prostheses. The present invention satisfies this need.

SUMMARY OF THE INVENTION

It is an object of the present invention to provide an anchoring or connecting structure for dental prostheses which absorbs a significant portion of the masticatory forces normally transmitted from the dentures to the underlying bone or tooth root.

It is another object of the present invention to provide an anchoring or connecting structure for dental prostheses which allows limited but substantially universal motion of the denture relative to the implant fixture anchoring it to the underlying bone or tooth root.

It is still another and more specific object of the present invention to provide a connector structure anchoring a denture to an underlying implant fixture, which absorbs a significant portion of the masticatory forces transmitted by the denture, and which allows limited but substantially universal motion of the denture relative to the underlying implant fixture.

It is yet another and more specific object of the present invention to provide a shock-absorbing connector structure for anchoring dentures to an underlying implant fixture, which can be utilized in conjunction with state of the art implant fixtures.

The foregoing and other objects and advantages are attained by a dental support structure having a first member which is attached to the jaw bone or tooth root through an implant fixture embedded in the bone or tooth root, and a second, keeper member to which a denture is attached. The second keeper member is removably mounted to the first member. A resilient, elastic member, such as an O ring, is disposed between the first member and the second, keeper member to permit limited but substantially universal motion of the keeper member relative to the first member, and to absorb forces transmitted by the denture through the keeper member towards the underlying bone or root structure.

The objects and features of the present invention are set forth in the appended claims. The present invention may be best understood by reference to the following description, taken in connection with the accompanying drawings wherein like numerals indicate like parts.

DESCRIPTION OF THE PREFERRED EMBODIMENTS

The following specification taken in conjunction with the drawings sets forth the preferred embodiment of the present invention. The embodiments of the invention disclosed herein are the best modes contemplated by the inventor for carrying out his invention in a commercial environment, although it should be understood that various modifications can be accomplished within the parameters of the present invention.

Figure 1:
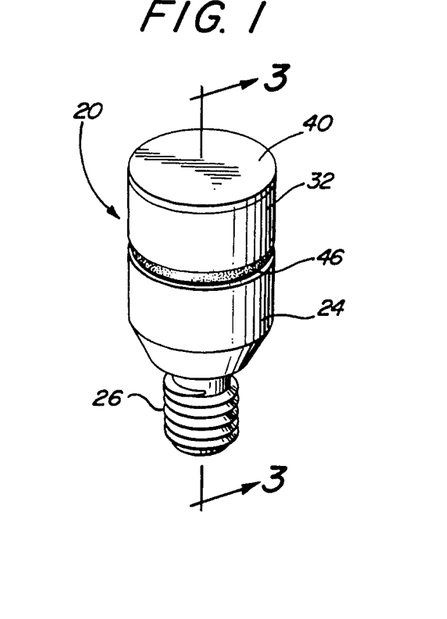
FIG. 1 is a perspective view of a first preferred embodiment of a dental connector of the present invention.
Figure 2:
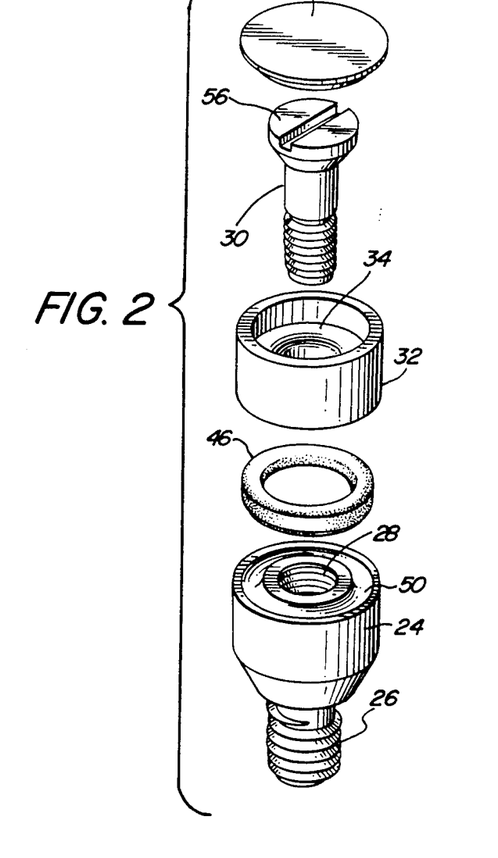
FIG. 2 is an exploded perspective view of the first preferred embodiment.
Figure 3:
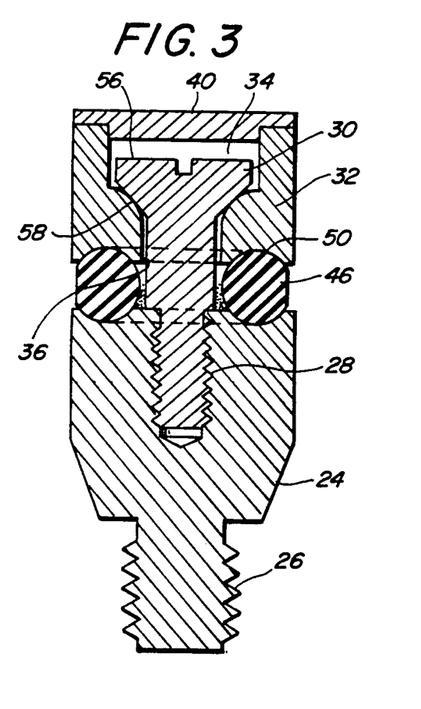
FIG. 3 is a cross-sectional view of the first preferred embodiment, the cross-section being taken on lines 3,3 of FIG. 1.

Referring now to the drawing Figures, and particularly to FIGS. 1 through 3, a first preferred embodiment 20 of the dental support structure of the present invention is disclosed. It should be noted at the outset of the present description that all of the herein described preferred embodiments of the dental support structures of the present invention are adapted to be affixed to implant fixtures of the type which are well known in the state-of-the art. As is known, such state-of-the-art implant fixtures usually comprise a titanium body embedded into the jaw bone or into tooth root of a person. The implant fixtures usually include an internal threaded opening into which the herein described dental support structures, or connectors, are mounted. Because the implant fixtures are state-of-the-art they are shown in the appended drawing Figures only schematically, for example as item 22 on FIGS. 10-13. Furthermore, as it known in the art, implant fixtures are implanted into the bone, or tooth root in a surgical procedure, after which there is a substantial time period, up to approximately one year, during which a healing process occurs. It is during this healing process that the implant fixture becomes embedded and accepted in the bone or tooth root.

Referring again primarily to FIGS. 1-3, the dental support structure or connector 20, includes a first member 24 which has a downwardly protruding substantially cylindrical threaded post 26. The threaded post 26 is utilized to mount the connector 20 to the implant fixture 22. The first member 24 is called, in accordance with usual practice in the art, a transmucosal cuff, and this terminology is used henceforth in the present description. The manner of affixing the transmucosal cuff 24 to the implant fixture 22 is not critical, instead of a threaded connection the transmucosal cuff 24 can also be cemented into the implant fixture 22.

The transmucosal cuff 24 includes an internal threaded opening 28. The threaded opening 28 receives a screw 30 which mounts a second or keeper member 32 to the transmucosal cuff 24. It will be readily understood by those skilled in the art that the transmucosal cuff 24 must be made of a material which is well adapted for implantation into the oral cavity. Titanium metal, and certain titanium alloys, which per se are well known in the art, are best suited for this purpose. Accordingly, the preferred embodiments of the transmucosal cuff 24 of the present invention are made from titanium or an alloy of titanium.

The keeper member 32 is also shown on FIGS. 1-3. It has a substantially cylindrical configuration, a hollow interior 34 and a hole or opening 36 in the bottom. A titanium screw 30 fits into the interior 34 of the keeper member 32, passes through the hole 36 and attaches the keeper member 32 to the transmucosal cuff 24. Instead of titanium the screw 30 can be made from other biocompatible materials, however titanium or titanium containing alloys are preferred.

The keeper member 32 of the first preferred embodiment is made from a material which comprises a magnetic alloy. Nobel magnetic alloy, such as cobalt palladium or CM 572 (made by Cendres & Metaux, S.A. Switzerland) is well suited, and is presently preferred for this purpose. The nobel metals reduce the possibility of stress and stress corrosion, crevis corrosion, fretting corrosion, galvanic corrosion, pitting and corrosion fatigue. See Chapter 1 "Corrosive Response of the Interface Tissue To ... (certain) Alloys" in a book entitled "The Dental Implant" by McKenney, Jr. and Lemons in American Academy of Implant Prosthodonics, copyright 1985 I.S.B.N. 0-88416-491-8.

Figure 10:
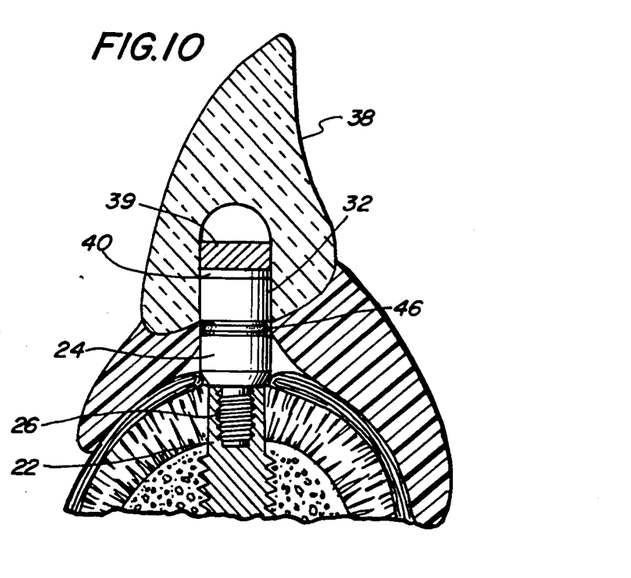
FIG. 10 is a schematic view of the first preferred embodiment carrying a denture.

Although certain improvements are described below in this connection, the magnetic properties of the keeper member 32 can be utilized, substantially in accordance with the state of the art to removably attach a denture 38 by means of a permanent magnet to the keeper member 32, as is shown on FIG. 10. In order to removably mount the denture 38 to the keeper member 32, the denture 38 includes a permanent magnet 39 disposed with open or closed field magnetic polarity to the magnetic alloy keeper member 32, so that the keeper 32 strongly attracts the magnet 39 embedded in the overdenture.

Figure 6:
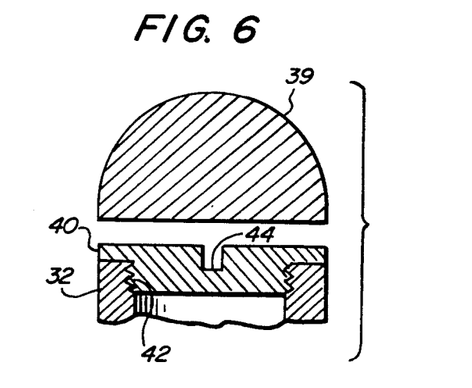
FIG. 6 is a partial cross-sectional view showing the top of a keeper member, and an interfacing magnet disposed in a denture mountable to the keeper member, in accordance with a fourth preferred embodiment of the present invention.

A cap or cover 40 preferably also made of the same magnetic material, such as Nobel magnetic alloy CM 572, is press fitted into the keeper member 32, so as to close the opening 34 when the keeper member 32 is assembled to the transmucosal cuff 24. In an alternative embodiment of the invention, shown on FIG. 6, the cap or cover 40 has a male threaded shoulder 42 which is mounted into matchingly threaded opening 28 of the keeper member 32. In this embodiment, the cap 40 includes a slot 44 to accept a screw driver (not shown) for assembly and disassembly and for the acceptance of the Shiner magnetic system (see U.S. Pat. No. 4,626,213).

Returning now again to the description of the first preferred embodiment, an important novel feature of the dental connector of the present invention is a resilient, elastic member 46 which is disposed between the adjoining, interfacing surfaces of the transmucosal cuff 24 and the keeper member 32. The resilient, elastic member 46, configured substantially as an O ring, performs important functions in the present invention.

First, the resilient member 46 acts as a shock or energy absorber, to dampen forces which are generated during mastication, and which are transmitted from the denture 38, through the keeper member 32 to the transmucosal cuff 24 and thence to the underlying bone or tooth root. As it is mentioned in the introductory section of the present application for patent, substantial forces (100 lbs and greater) are generated during normal mastication. Whereas normal healthy teeth, gum and bone tissue are capable of resiliently absorbing these forces, prior art rigid dentures do not absorb them, with adverse consequences to the patient.

The resilient member or O ring of the herein described preferred embodiment is preferably made of silicone rubber. It can be made from other resilient plastic materials, the requirements in this connection are merely that the material must be compatible with implantation into the oral cavity, and must provide such resiliency that approximately 0 to 0.4 mm compression of the O ring occurs during normal masticatory load forces, so that the keeper member 32 moves within a range of approximately 0 to 0.4 mm relative to the transmucosal cuff 24.

The screw 30 controls the height of the keeper 32 with respect to the cuff 24. The length of the screw 30 may also vary to provide an additional selected range of motion. The resiliency of the O-ring 46 may also be varied for controlling the range of movement in combination with or independently of the length of the screw 30.

A second function of the O-ring 46 is to permit universal "rocking" motion of keeper member 32 relative to the transmucosal cuff 24. In other words, the O-ring 46 functions to permit limited, but universal motion of the keeper member 32 relative to the transmucosal cuff 24. Simple up-and-down motion of keeper member 32 while compressing the O ring 46 is illustrated on FIG. 7 of the appended drawings, whereas "rocking" universal motion is illustrated on FIG. 8. The herein described preferred embodiments of the O-ring has a substantially flattened exterior wall 48, so as not to be pinched as is shown on the drawings.

It is emphasized in connection with the above-noted functions of the resilient member, O ring 46 in the dental connector structure of the invention, that these functions and the herein described structure is significantly different from the functions and structure described in U.S. Pat. No. 4,204,321. In that prior art patent, an elastomeric O ring is used in a dental post to apply retentive force and secure a denture to the post.

Figure 7:
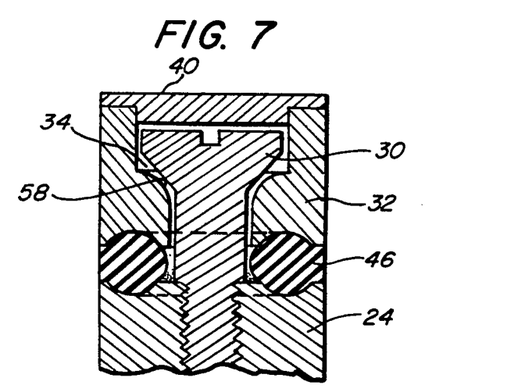
FIG. 7 is a cross-sectional view of the first preferred embodiment, the view showing a resilient O ring member in a compressed state.
Figure 8:
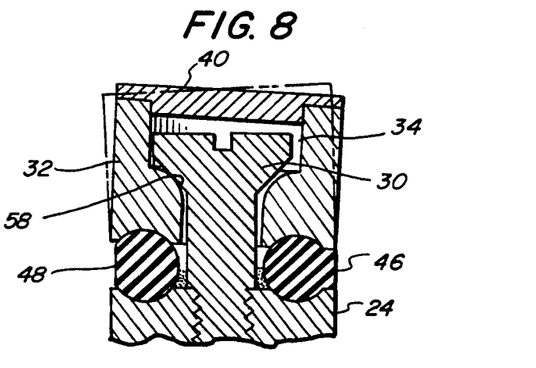
FIG. 8 is another cross-sectional view of the first preferred embodiment, the view showing rocking motion of a keeper member relative to a first, transmucosal cuff member.

In order to disassemble the dental connector of the present invention, the cap or cover 40 must be first removed to gain access to the screw 30. In the first preferred embodiment, this can be accomplished by the dentist or oral surgeon (not shown) strongly pushing down on the keeper member 32 until the head of the screw 30 pushes against and lifts off the press-fitted cap 40 or the cap may be unscrewed as per FIG. 6. FIG. 7 illustrates the the O ring 46 in a compressed position, and the screw head approaching the position wherein the cover 40 is about to be touched and lifted off from the keeper member 32.

It should be understood in connection with the present invention, that the resiliency of the resilient member 46 may be adjusted to fit particular requirements of a patient. Furthermore, as it was mentioned above, it takes substantial time after surgical implantation for the implant fixtures 22 to become accepted in the underlying bone or tooth root, and therefore for these fixtures to reach their maximum load bearing capacity. See the article in CDA Journal, October 1987 by W. Eugene Roberts, D.D.S., Ph.D et al. entitled "Bone Physiology and Metabolism". The article emphasizes the need for stress reduction during the maturation phase of the healing bone. In light of the foregoing, it is often desirable after implantive surgery to increase the load only gradually over a period of several months on the implanted fixtures 22. This can be accomplished in accordance with the present invention by either gradually changing, after implantive surgery, the resiliency of the O rings 46, or by using different lengths of the screw 30 to restrict the compressive travel of the O ring so as not to exceed a desired load force on the O ring.

The exploded view of FIG. 2 illustrates grooves or recesses 50 disposed in the respective surfaces of the transmucosal cuff 24 and the keeper member 32, which provide a gland for the O ring 46.

The manner in which the denture 38 is mounted to the keeper member 32 is not critical for the purposes of the present invention. Although magnetic mounting, which can be accomplished in accordance with the state-of-the-art, is preferred, mechanical mounting of the denture 38 to the keeper member 32 is also possible while practicing the present invention.

Figure 4:
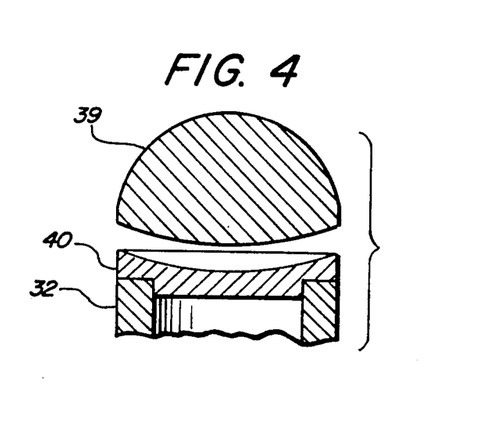
FIG. 4 is a partial cross-sectional view showing the top of a keeper member, and an interfacing magnet disposed in a denture mountable to the keeper member, in accordance with a second preferred embodiment of the present invention.
Figure 5:
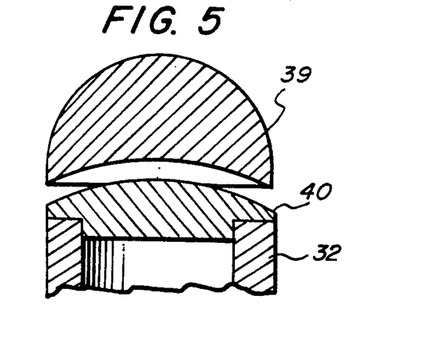
FIG. 5 is a partial cross-sectional view showing the top of a keeper member, and an interfacing magnet disposed in a denture mountable to the keeper member, in accordance with a third preferred embodiment of the present invention.

FIGS. 4, and 5 illustrate alternative embodiments with respect to the manner of magnetically mounting the denture 38 to the keeper member 32. In the embodiments shown in FIGS. 4 and 5, the cap 40 has convex or concave curvature respectively, and a permanent magnet 39 of the denture 38 has a curvature complementary to the curvature of the cap 40.

Figure 11:
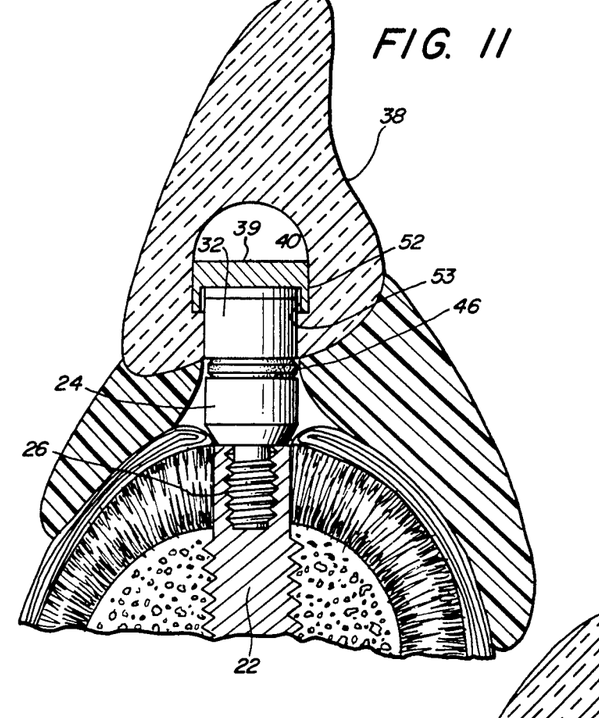
FIG. 11 is schematic view of a sixth preferred embodiment, carrying a denture.

FIG. 11 illustrates still another embodiment, wherein the denture is mounted by magnetic means to the keeper member 32, and wherein the second magnet 39 of the denture 38 has a skirt 52. The skirt 52 surrounds the upper portion of the keeper member 32 to prevent or limit lateral movement of the denture 38 on the keeper 32. A small clearance 53 is provided between the skirt 52 and the top of the keeper 32 to allow the denture to be readily fitted to the keeper member 32.

The downwardly extending skirt 52 must provide a skirt clearance to the keeper assembly (32 to 40) to allow insertion of the overdenture. The downwardly extending skirt 52 can be a part of the original magnet housing 39 or a retrofit to existing magnet housings.

Figure 9:
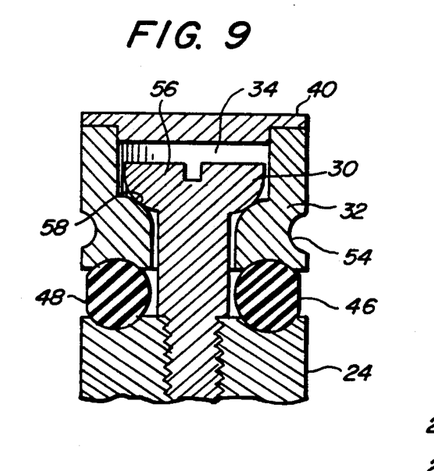
FIG. 9 is a cross-sectional view of a fifth preferred embodiment.

FIG. 9 illustrates yet another embodiment of the dental connector of the present invention. In this embodiment the keeper member 32 is not made of a magnetic alloy. Rather it is made from a suitable gold alloy, such as CERAMICOR. In this embodiment the denture 38 is mounted to the keeper 32 by mechanical means, such as casting a portion (not shown) of the denture 38 about the keeper 32. An annular recess 54 shown on FIG. 9 in the side wall of the cylindrical keeper 32 of this embodiment serves to locate during assembly and increase the strength with which the casting (not shown) around the keeper 32 adheres to the keeper 32.

The embodiment shown on FIG. 9 illustrates yet another novel feature of the invention. In this embodiment the surface of the head 56 of the screw 30 is curved, opposite to the curvature of the interior surface 58 of the keeper member 32 so as to minimize the contact area between the screw 30 and adjoining curved surface 58 of the keeper member 32. The just described configuration facilitates the universal joint type action of the O ring 46, in permitting facile movement of the keeper member 32 relative to the transmucosal cuff 24.

Referring back to FIGS. 1–3 and 7 and 8 which illustrate the first preferred embodiment, the interior surface 58 of the keeper member 32 is curved in the same manner as in the embodiment illustrated in FIG. 9. Although the adjoining surface of the screw head 56 is flat in this embodiment, still, only a relatively small contact area (theoretically only a contact line) exists between the screw 30 and the keeper member 32. This is an advantage, because the contact is between two different metals (the screw 30 is titanium, the keeper member 32 is a magnetic alloy), so that minimal contact is desirable to minimize possible corrosion of these components.

The fact that the transmucosal cuff 24 and the keeper member 32 are separated from one another by the resilient member 46 in accordance with the invention, is a further advantage over prior art, in that the separation of these components further avoids undesirable corrosion when these two parts are made from different metals.

In alternative embodiments (not shown) the surface of the screw head 56 used in magnetic keeper members 32 also has a curvature of the opposite kind of the curvature of the interior surface 58 of keeper member 32. This further minimizes contact between the titanium screw and the magnetic metal keeper 32, and thereby further minimizes corrosion.

Figures 12, 13:
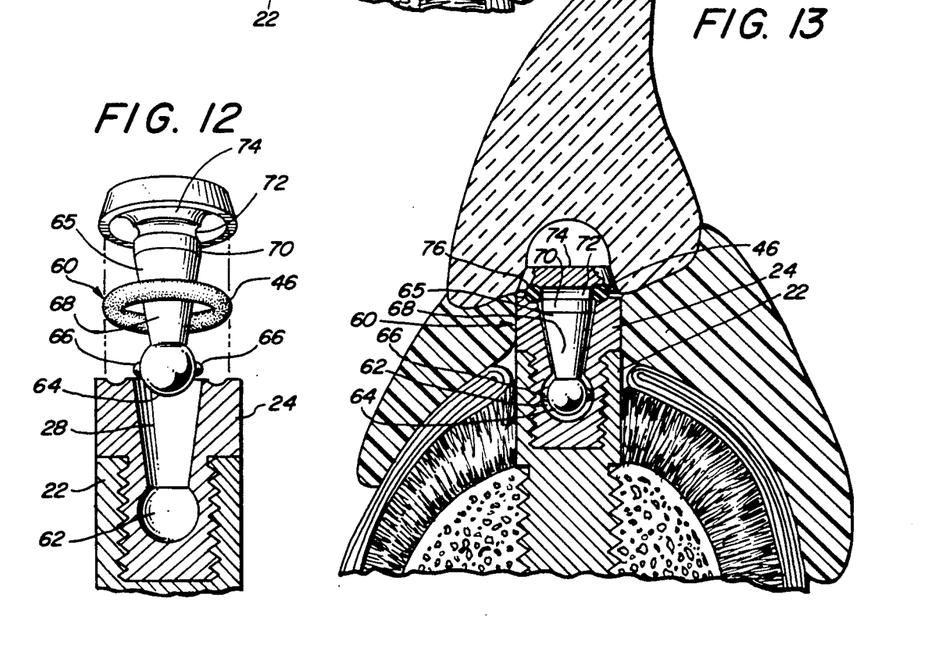
FIG. 12 is a partially exploded perspective view of a seventh preferred embodiment.
FIG. 13 is a schematic view of the seventh preferred embodiment, caring a denture.

Referring now to FIGS. 12 and 13, yet another preferred embodiment 60 of the dental connector or support structure of the present invention is shown. This embodiment is designed to be analogous to the dental connector commonly known in the art under the ZEST mark, and is capable of being mounted into the same type of implant fixture 22 as a ZEST connector.

The embodiment 60 includes a transmucosal cuff 24 having a cavity 28 which forms a socket 62 for a ball type end 64 of a post 65 of a matching keeper member 32. The ball type end 64 includes mechanically extended retainer balls 66. A portion 68 of the post 65 is conical, and there is a cylindrical portion 70 above the conical portion 68. An annular recess 72 is disposed in the cylindrical portion 70 to serve as a gland for the resilient O ring member 46. A top part 74 of the keeper member 32 accepts a strong permanent magnet to attach a denture (not shown on FIGS. 12 and 13), in the manner well known in the art. An undersurface 76 of the magnetic top part 74 of the keeper 32 is also curved to form a gland to accommodate the O ring 46. The function and purpose of the resilient O ring member 46 in this embodiment is substantially the same as in the other above-described embodiments with the ability to control the resiliency by changing the O-rings.

Several modifications of the above-described invention may become readily apparent to those skilled in the art in light of the disclosure. Therefore, the scope of the present invention should be interpreted solely from the following claims, as such claims are read in light of the disclosure.

What is claimed is:

1. A dental connector adapted to be secured to an implant fixture embedded in a patient's jaw bone or tooth root, for providing support to a denture or overdenture attached to the connector, the connector comprising:

a transmucosal cuff adapted to be removably secured to the implant fixture, the cuff including a threaded portion;

a keeper member having an internal bore through which a screw extends, the screw engaging the threaded portion on the cuff to secure the cuff and the keeper member together, and cuff and keeper member having opposed annular concave grooves with the cross-sectional surfaces of said grooves following a circular arc;

a resilient O-ring disposed between the cuff and the keeper member and within the annular grooves thereof, the O-ring acting as means for absorbing forces transmitted by the keeper member to the cuff and as means for permitting limited but substantially universal motion between the keeper member and the cuff, thereby cushioning the underlying implant fixture, bone or tooth root from forces transmitted by the denture or overdenture, the surfaces of the annular grooves in the cuff and keeper member being in intimate contact with the O-ring as the keeper member is moved relatively to the cuff; and means included in the keeper member for removably connecting an overlaying denture including a false tooth, to the keeper member.

2. The dental connector of claim 1 wherein the O ring comprises silicone rubber.

3. The dental connector of claim 2 wherein the O ring permits infinite travel of the keeper member relative to the cuff within the range of 0 to 0.4 mm under the forces normally generated during normal use of the denture.

4. The dental connector of claim 3 wherein the last named means comprise magnetic means.

5. The dental connector of claim 3 wherein the last named means comprise mechanical means.

6. The dental connector of claim 3 wherein the bore of the keeper member includes a curved wall configured to form substantially tangential contact with the head of the screw, and wherein the curved wall forms the only contact of the screw with the keeper member.

7. The dental connector of claim 6 wherein the head of the screw also has a curved wall of the opposite curvature to the curved wall of the bore.

8. The dental connector of claim 1 further comprising a removable cap which is press-fitted into the keeper member to close the bore and cover the screw within the keeper member.

9. A dental support structure adapted for attachment to an implant fixture which is implanted in a patient's jaw bone or in a tooth root, the support structure providing a support to a denture attachable to the support structure, the support structure comprising:

a transmucosal cuff comprising a downwardly projecting threaded end, the threaded end being removably mounted in the implant fixture, the cuff having an internally threaded opening;

a cylindrical keeper member having an upper portion and an internal bore extending therethrough for receiving a screw;

a screw of predetermined length for insertion through the bore in the keeper member and into the threaded opening in the cuff to releasably secure the keeper cylindrical member to the cuff, the cuff and keeper member having opposed annular concave grooves with the cross-sectional surfaces of said grooves following a circular arc;

magnetic means carried by the keeper member for releasably retaining an overlaying denture, including a false tooth, to the keeper cylindrical member;

a resilient O-ring disposed between the cuff and the keeper cylindrical member and within the annular grooves thereof, the O-ring serving as means for keeping the cuff and the keeper cylindrical member from being in direct contact with one another, for allowing limited but substantially universal motion between the cuff and the keeper cylindrical member and for cushioning the cuff and a patient's underlying bone or tooth root from mastication forces transmitted through the keeper member, the surfaces of the annular grooves in the cuff and keeper member being in intimate contact with the O-ring prior to and during the application of mastication forces to the keeper member;

said O-ring having a substantially flattened wall adjoining a direction of displacement so as to avoid pinching of said compressible member resulting from movement of said keeper member relative to said cuff; and said magnetic means including a magnetic piece attached to the overlaying denture having a downwardly protruding skirt configured to surround the upper portion of the keeper member to limit the lateral movement of the denture on the keeper member.

10. The dental support structure of claim 9 wherein the resilient O-ring comprises silicone rubber.

11. The dental support structure of claim 9 wherein the resilient O-ring permits a maximum of approximately 0.1 to 0.4 mm movement of the keeper cylindrical member relative to the cuff under load conditions which occur during normal use of the support structure.

12. The dental support structure of claim 9 further comprising a removable cap press-fitted into the keeper cylindrical member to close the internal opening.

13. The dental support structure of claim 12 wherein the internal opening of the keeper cylinder member, the screw and the cap are dimensioned in such a manner that pressing the keeper cylindrical member downwards towards the cuff while compressing the resilient O-ring pushes the screw upwardly against the cap and removes the cap from its position in the keeper cylinder member.

14. The dental support structure of claim 9 wherein the internal opening of the keeper member includes a curved wall configured to form substantially only line contact with the head of the screw, and wherein the curved wall forms the only contact of the screw with the keeper member.

15. The dental support structure of claim 14 wherein the head of the screw also has a curved wall of opposite curvature to the curved wall of the bore, thereby further minimizing contact area between the screw and the keeper member.

16. The dental support structure of claim 9 wherein the resilient O-ring is adapted for allowing a selected range of approximately 0.0 to 0.4 mm movement of the cylindrical member relative to the cuff under normal use of the denture.

17. A dental support structure adapted for attachment to an implant fixture which is implanted in a patient's jaw bone or in a tooth root, the support structure providing a support with a selectable degree of resiliency to a denture attachable to the support structure during the time that the jaw is healing and accommodating the implant, the support structure comprising:

a transmucosal cuff comprising a downwardly projecting threaded end, the threaded end being removably mounted in the implant fixture, the cuff having an internally threaded opening;

a cylindrical keeper member having an internal bore extending therethrough for accommodating a screw;

a screw of predetermined length for insertion through the bore in the keeper member and into the threaded opening in the cuff to releasably secure the keeper member to the cuff;

means carried by the keeper member for attaching an overlaying denture, including a false tooth, to the keeper member; and a plurality of interchangeable O-rings, each O-ring having a different degree of resiliency, the cuff and keeper member having opposed annular concave grooves with the cross-sectional surfaces of said grooves following a circular arc for receiving one of said O-rings with the selected resiliency, the O-ring preventing the cuff and the keeper cylindrical member from being in direct contact with one another while allowing limited but substantially universal motion between the cuff and the keeper member and cushioning with a selected degree of resiliency the cuff and a patient's underlying bone or tooth root from mastication forces transmitted through the keeper member, the screw maintaining a constant vertical relationship of the jaw in the absence of mastication forces.

18. A method of connecting and retaining dentures following implantive surgery so as to provide a gradually increasing load from masticatory forces onto an implant fixtrue embedded within a patient's jaw bone during the healing process comprising:
 a. providing a connector assembly adapted to be secured to the implant fixture, the connector assembly having means for removably connecting an overlaying denture and for receiving a resilient O-ring for cushioning the implant fixture from masticatory forces applied to the connector assembly from the denture including a screw of predetermined length to maintain a constant vertical relationship between the implant fixture and the denture in the absence of mastication forces;
 b. providing a plurality of resilient O-rings, each having a different modulus of elasticity;
 c. selecting one of said O-rings having a desired modulus of elasticity;
 d. installing the O-ring selected in step c within said connector assembly so as to cushion the implant fixture from masticatory forces;
 e. removing the O-ring from said connector assembly following a period of bone healing;
 f. installing a selected one of said O-rings having a modulus of elasticity less than that of the O-ring removed in step e; and
 g. repeating steps e and f until a selected one of said O-rings having a desired modulus of elasticity is installed upon completion of bone healing.

* * * * *

UNITED STATES PATENT AND TRADEMARK OFFICE
CERTIFICATE OF CORRECTION

PATENT NO. : 4,993,950

DATED : February 19, 1991

INVENTOR(S) : Merrill C. Mensor Jr.

It is certified that error appears in the above-identified patent and that said Letters Patent is hereby corrected as shown below:

Column 1, line 6, "208,324" should read --209,324.

Column 4, line 35, "it" should read --is--.

Signed and Sealed this

Third Day of November, 1992

Attest:

DOUGLAS B. COMER

Attesting Officer

Acting Commissioner of Patents and Trademarks